United States Patent [19]

Meazza et al.

[11] Patent Number: 5,721,192
[45] Date of Patent: Feb. 24, 1998

[54] AMINOSULFONYL UREAS

[75] Inventors: Giovanni Meazza, Saronno; Giampaolo Zanardi, Vigevano; Sergio Massimini, Milan; Piero La Porta, Novara; Ernesto Signorini, Malnate, all of Italy

[73] Assignee: Isagro Ricerca S.r.l., Milan, Italy

[21] Appl. No.: 733,145

[22] Filed: Oct. 16, 1996

[30] Foreign Application Priority Data

Oct. 27, 1995 [IT] Italy ................... MI95A2215

[51] Int. Cl.⁶ .................. C07D 239/32; A01N 47/36
[52] U.S. Cl. ................... 504/214; 544/321; 544/332
[58] Field of Search ................... 544/321, 332; 504/214

[56] References Cited

U.S. PATENT DOCUMENTS

| | | | |
|---|---|---|---|
| 4,515,620 | 5/1985 | Böhner | 71/91 |
| 4,559,081 | 12/1985 | Van Gemert | 71/93 |
| 4,622,065 | 11/1986 | Van Gemert | 71/93 |
| 4,666,508 | 5/1987 | Van Gemert | 71/93 |
| 4,696,695 | 9/1987 | Gemert | 71/92 |
| 4,741,762 | 5/1988 | Van Gemert | 71/92 |
| 5,280,007 | 1/1994 | Kawai | 504/105 |
| 5,492,884 | 2/1996 | Condon et al. | 504/214 |

OTHER PUBLICATIONS

Database WPI, Derwent Publications, AN 95–180022, JP–A–07188184, Jul. 25, 1995.
Chemical Abstract, 99:53793, 1983.

*Primary Examiner*—Matthew V. Grumbling
*Assistant Examiner*—Deepak R. Rao
*Attorney, Agent, or Firm*—Oblon, Spivak, McClelland, Maier & Neustadt, P.C.

[57] ABSTRACT

Aminosulfonyl ureas having general formula (I):

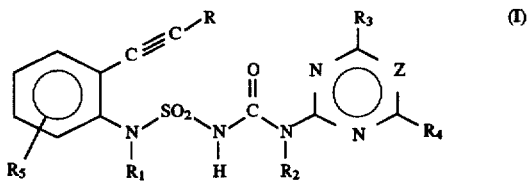

The aminosulfonyl ureas having general formula (I) have a high herbicidal activity.

18 Claims, No Drawings

AMINOSULFONYL UREAS

The present invention relates to new aminosulfonyl ureas.

More specifically the present invention relates to aminosulfonyl ureas having a high herbicidal activity, a process for their preparation and their use as herbicides for the control of weeds.

Aminosulfonyl ureas having a herbicidal activity are described in U.S. Pat. Nos. 4,515,620, 4,622,065, 4,666,508, 4,696,695 and 4,741,762. These products however are not very selective as they are generally toxic also towards the most important agricultural cultivations.

The Applicant has now found new aminosulfonyl ureas which, as well as having a high herbicidal activity against numerous kinds of weeds, also have a low phytotoxicity for one or more cultivations of greatest agricultural interest and can therefore be used as selective herbicides.

The present invention therefore relates to aminosulfonylureas having general formula (I):

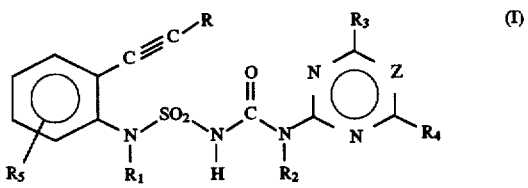

wherein:

R represents a hydrogen atom; a halogen atom such as chlorine, fluorine, bromine or iodine; a $C_1$–$C_8$ alkyl or haloalkyl group, linear or branched; a $C_3$–$C_6$ cycloalkyl or halocycloalkyl group; a $C_4$–$C_8$ cycloalkylalkyl or halocycloalkylalkyl group; $C_2$–$C_8$ alkoxyalkyl or haloalkoxyalkyl group, linear or branched; a $C_2$–$C_8$ alkylthioalkyl or haloalkylthioalkyl group, linear or branched; a $C_2$–$C_8$ alkoxycarbonyl or haloalkoxycarbonyl group, linear or branched; $C_2$–$C_8$ alkylaminocarbonyl group, linear or branched; a $C_3$–$C_8$ dialkylaminocarbonyl group; a $C_2$–$C_8$ alkylcarbonyl or haloalkylcarbonyl group, linear or branched; a $C_3$–$C_9$ trialkylsilyl group; a phenyl group optionally substituted by halogens such as chlorine, fluorine, bromine or iodine, by $C_1$–$C_4$ alkyl or haloalkyl groups, linear or branched, by $C_1$–$C_4$ alkoxy or haloalkoxy groups, linear or branched, by $C_1$–$C_4$ alkylthio or haloalkylthio groups, linear or branched;

$R_1$ and $R_2$ each independently represent, a hydrogen atom; a $C_1$–$C_4$ alkyl or haloalkyl group, linear or branched; a $C_3$–$C_6$ alkoxyalkyl or haloalkoxyalkyl group, linear or branched; a $C_3$–$C_6$ alkenyl or haloalkenyl group, linear or branched; a $C_3$–$C_6$ alkynyl or haloalkynyl group, linear or branched;

$R_3$ and $R_4$ each independently represent, a hydrogen atom; a halogen atom such as chlorine, fluorine, bromine or iodine; a $C_1$–$C_6$ alkyl or haloalkyl group, linear or branched; a $C_1$–$C_6$ alkoxy or haloalkoxy group, linear or branched; a $C_1$–$C_6$ alkylamine group, linear or branched; a $C_2$–$C_8$ dialkylamine group, linear or branched; a $C_3$–$C_6$ cycloalkyl or cycloalkoxy group; a $C_4$–$C_7$ cycloalkylalkyl or cycloalkylalkoxy group;

$R_5$ represents a hydrogen atom; a halogen atom such as chlorine, fluorine, bromine or iodine; a $C_1$–$C_4$ alkyl or haloalkyl group, linear or branched; a $C_1$–$C_4$ alkoxy or haloalkoxy group, linear or branched;

Z represents a nitrogen atom or a CH group.

The aminosulfonyl ureas having general formula (I) have a high herbicidal activity.

Specific examples of aminosulfonyl ureas having general formula (I) which are interesting for their herbicidal activity are:

N-[2-(3,3,3-trifluoropropynyl)-phenyl]-aminosulfonyl-N'-(4-methoxy-6-methyl-1,3,5-triazin-2-yl) urea;

N-[2-(3,3,3-trifluoropropynyl)phenyl]-aminosulfonyl-N'-(4,6-dimethoxypyrimidin-2-yl)urea;

N-(2-chloroethynylphenyl)-aminosulfonyl-N'-(4-methoxy-6-methyl-1,2,5-triazin-2-yl)urea;

N-(2-chloroethynylphenyl)-aminosulfonyl-N'-(4,6-dimethoxypyrimidin-2-yl)urea;

N-(2-bromoethynylphenyl)-aminosulfonyl-N'-(4-methoxy-6-methyl-1,3,5-triazin-2-yl)urea;

N-(2-bromoethynylphenyl)-aminosulfonyl-N'-(4,6-dimethoxypyrimidin-2-yl)urea;

N-(2-ethynylphenyl-aminosulfonyl-N'-(4-methoxy-6-methyl-1,3,5-triazin-2-yl)urea;

N-(2-ethynylphenyl)-aminosulfonyl-N'-(4,6-dimethoxypyrimidin-2-yl)urea;

N-[2-(propyn-1-yl)-phenyl]-aminosulfonyl-N'-(4-methoxy-6-methyl-1,3,5-triazin-2-yl)urea;

N-[2-(propyn-1-yl)phenyl]aminosulfonyl-N'-(4,6-dimethoxypyrimidin-2-yl)urea;

N-[2-(3-methoxypropyn-1-yl)-phenyl]-aminosulfonyl-N'-(4-methoxy-6-methyl-1,3,5-triazin-2-yl)urea;

N-[2-(3-methoxypropyn-1-yl)-phenyl]-aminosulfonyl-N'-(4,6-dimethoxypyrimidin-2-yl)urea;

N-[2-(3-ethoxypropyn-1-yl)-phenyl]-aminosulfonyl-N'-(4-methoxy-6-methyl-1,3,5-triazin-2-yl)urea;

N-[2-(3-ethoxypropyn-1-yl)-phenyl]-aminosulfonyl-N'-(4,6-dimethoxypyrimidin-2-yl)urea N-[2-(methoxycarbonylethynyl)phenyl]-aminosulfonyl-N'-(4-methoxy-6-methyl-1,3,5-triazin-2-yl)urea;

N-[2-(methoxycarbonylethynyl-1-yl)phenyl]-aminosulfonyl-N'-(4,6-dimethoxypyrimidin-2-yl urea;

N-[2-(dimethylaminocarbonylethynyl)phenyl] aminosulfonyl-N'-(4-methoxy-6-methyl-1,3,5-triazin-2-yl) urea;

N-[2-(3-methoxycarbonylethynyl)phenyl]-aminosulfonyl-N'-(4,6-dimethoxypyrimidin-2-yl)urea.

The aminosulfonyl ureas having general formula (I) of the present invention have an acidic nature and can therefore form salts with basic substances such as, for example, hydroxides of alkaline and earth-alkaline metals, amines and other organic bases, quaternary ammonium salts.

A further object included in the scope of the present invention relates to the use of the aminosulfonyl ureas having general formula (I) both in their free form and in their salified form.

Another object of the present invention is a process for the preparation of the compounds having general formula (I).

The compounds having general formula (I) can be obtained with a process comprising:

(a) reacting a heterocyclic amine having general formula (II):

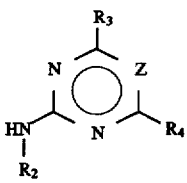

wherein $R_2$, $R_3$, $R_4$ and Z have the same meaning defined above, with a halosulfonylisocyanate having general formula (III):

wherein X represents a halogen atom such as, for example, chlorine, fluorine, bromine, preferably chlorine, in the presence of an inert organic solvent, obtaining a halosulfamoyl urea having general formula (IV):

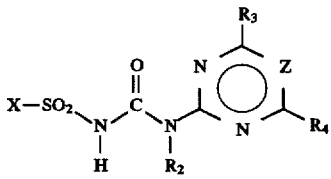

wherein X, $R_2$, $R_3$, $R_4$, and Z have the same meaning defined above;

(b) reacting the halosulfamoylurea having general formula (IV) obtained in step (a) with an aniline having general formula (V):

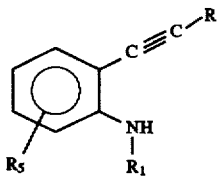

wherein R, $R_1$ and $R_5$, have the same meaning defined above, in the presence of or without a base, preferably in the presence of a base, and an inert organic solvent.

Inert organic solvents which can be used in steps (a) and (b) of the process described above are aromatic hydrocarbons (such as, for example, benzene, toluene, xylene, etc.), chlorinated hydrocarbons (such as, for example, methylene chloride, chloroform, carbon tetrachloride, chlorobenzene, etc.), ethers (such as, for example, ethyl ether, dimethoxyethane, tetrahydrofuran, dioxane, etc.).

Bases which can be used in step (b) of the above process are organic bases, preferably aliphatic amines such as, for example, triethylamine, etc.

The above steps (a) and (b) are carried out at temperatures of between $-70°$ C. and the boiling point of the solvent used, preferably between $-20°$ C. and $30°$ C.

The reaction of step (b), between the aniline having general formula (V) and the halosulfamoyl urea having general formula (IV), can be conveniently carried out without isolating said halosulfamoyl urea (IV), by directly adding the aniline (V) and the base (diluted with the same inert organic solvent used in step (a) of the above process) operating in the same environment as the first passage.

The heterocyclic amines having general formula (II) and halosulfonylisocyanates having general formula (III) are compounds known in the art.

The anilines having general formula (V) can be prepared by adapting the known methods described in literature such as, for example, by L. Brandsma in "Preparative Acetylenic Chemistry" (1988), II° Edition, Ed. Elsevier-Amsterdam, to the particular substrates necessary. More specifically, the aniline having general formula (V) can be prepared following the procedures described in: "Journal Fluorine Chemistry" (1991), Vol. 55, pages 199–206 and "Journal Fluorine Chemistry" (1987), Vol. 36, pages 313–317.

The compounds having general formula (I), of the present invention have shown interesting biological activities and, in particular, a high herbicidal activity which makes them suitable for use in agriculture in defending useful crops from weeds.

In particular, the compounds having general formula (I) are efficient in the control, both in pre-emergence and post-emergence, of numerous monocotyledon and dicotyledon weeds. At the same time, these compounds are compatible or have no toxic effects with respect to useful crops, both in pre-emergence and post-emergence treatment.

Examples of weeds which can be effectively controlled using the compounds having general formula (I) of the present invention are: Sorghum Halepense, Echinocloa crusqalli, Arena fatua, Amni maius, Abutilon theofrasti, Stellaria media, Convolvulus sepium, Amaranthus retroflexus, Chenopodium alba, Galium aparine, Senecio vulgaris, Alopercurus myosuroides, Cyperus spp., etc.

With the dosages used for agricultural applications, the above compounds have shown no toxic effects towards important agricultural crops such as rice (Oryza satira), wheat (Triticum spp.), maize (Zea mais), soybean (Glycine max), etc.

A further object of the present invention relates to a method for controlling weeds in cultivated areas by the application of the compounds having general formula (I).

The quantity of compound to be applied to obtain the desired effect can vary depending on different factors such as, for example, the compound used, the crop to be preserved, the weed to be eliminated, the degree of infestation, climatic conditions, characteristics of the soil, method of application, etc.

Dosages of compound of between 5 g and 5000 g per hectare generally provide sufficient control.

For practical uses in agriculture it is often advantageous to use compositions with a herbicidal activity containing, as active substance, one or more compounds having general formula (I).

It is possible to use compositions in the form of dry powders, wettable powders, emulsifiable concentrates, microemulsions, pastes, granules, solutions, suspensions etc.: the selection of the type of composition will depend on the specific use.

The compositions are prepared according to the known methods, for example by diluting or dissolving the active substance with a solvent and/or solid diluent, possibly in the presence of surfactants.

As solid inert diluents, or carriers, it is possible to use kaolin, alumina, silica, talc, bentonite, chalk, quartz, dolomite, attapulgite, montmorillonite, diatomaceous earth, cellulose, starch, etc.

As liquid inert diluents, in addition to water obviously, it is possible to use organic solvents such as aromatic hydrocarbons (xylols, mixtures of alkylbenzols, etc.), aliphatic hydrocarbons (hexane, cyclohexane, etc.), halogenated aromatic hydrocarbons (chlorobenzol, etc.), alcohols (methanol, propanol, butanol, octanol, etc.), esters (isobutyl acetate, etc.), ketones (acetone, cyclohexanone, acetophenone, isophorone, ethylamylketone, etc.) or vegetable or mineral oils or their mixtures.

As surfactants it is possible to use wetting and emulsifying agents of the non-ionic type (polyethoxylated alkylphenols, polyethoxylated fatty alcohols, etc.), anionic type (alkylbenzenesulfonates, alkylsulfonates, etc.), cationic type (quaternary salts of alkylammonium, etc.).

It is also possible to add dispersing agents (for example lignin and its salts, derivatives of cellulose, alginates, etc.), stabilizers (for example anti-oxidants, ultraviolet-ray absorbers, etc.).

To increase the range of action of the above compositions, other active ingredients can also be added such as, for example, other herbicides, fungicides, insecticides or acaricides, fertilizers.

The concentration of active substance in the above compositions can vary within a wide range, depending on the active compound, the applications for which they are destined, environmental conditions and type of formulation adopted.

The concentration of active substance is generally between 1% and 90%, preferably between 5% and 50%.

The following examples are illustrative and do not limit the scope of the present invention.

EXAMPLE 1

Preparation of N-[2-(3,3,3-trifluoropropynyl)-phenyl]aminosulfonyl-N,-(4-methoxy-6-methyl-1,3,5-triazin-2-yl)urea (Compound Nr 1)

0.71 g (5 mmoles) of chlorosulfonylisocyanate are slowly added dropwise, in an atmosphere of nitrogen, to a suspension of 0.70 g (5 mmoles) of 2-amino-4-methoxy-6-methyl-1,3,5-triazine in 25 ml of tetrahydrofuran cooled to −5° C. The mixture is maintained under stirring at room temperature for 8 hours.

Subsequently a solution of 0.93 g (5 mmoles) of 2-(3,3,3-trifluoropropynyl)-aniline and 0.73 ml (5.2 mmoles) of triethylamine in 5 ml of tetrahydrofuran is added and the mixture is maintained under stirring for a further 3 hours at room temperature. It is poured into water (150 ml) and extracted with methylene chloride (3×30 ml).

The organic phase is then washed again with water, anhydrified with sodium sulfate and concentrated. The raw product is purified by silica gel chromatography eluating with methylene chloride/acetone in a ratio of 9:1.

1.13 g of a yellow solid are obtained which is further purified by crushing with hexane/ethyl ether/ethyl acetate in a ratio of 4:1:1. 0.95 g of a solid are obtained from this purification corresponding to Compound Nr 1 having a melting point of 98° C.

EXAMPLE 2

Preparation of N-[2-(3,3,3-trifluoropropynyl)-phenyl]aminosulfonyl-N'-(4,6-dimethoxy-pyrlmidin-2-yl)urea (Compound Nr 2)

Using a similar procedure to that described in example 1, starting from 0.93 g (5 mmoles) of 2-(3,3,3-trifluoropropynyl)aniline and 0.78 g (5 mmoles) of 2-amino-4,6-dimethoxypyrimidine, 1.2 g of a solid were obtained corresponding to Compound Nr 2 having a melting point of 144° C.–145° C.

EXAMPLE 3

Following the procedure described in Example 1, the following compounds were also prepared:

N-(2-ethynylphenyl)-aminosulfonyl-N'-(4-methoxy-6-methyl-1,3,5-triazin-2-yl)urea (Compound Nr 3) having a melting point of 132° C.;

N-(2-ethynylphenyl)-aminosulfonyl-N'-(4,6-dimethoxypyrimidin-2-yl)urea (Compound Nr 4) having a melting point of 151° C.;

N-(2-chloroethynylphenyl)-aminosulfonyl-N'-(4-methoxy-6-methyl-1,3,5-triazin-2-yl)urea (Compound Nr 5) having a melting point of 143° C.;

N-(2-chloroethynylphenyl)-aminosulfonyl-N'-(4,6-dimethoxypyrimidin-2-yl)urea (Compound Nr 6) having a melting point of 163° C.;

N-[2-(3-methoxy-1-propyn-1-yl)phenyl]aminosulfonyl-N'-(4-methoxy-6-methyl-1,3,5-triazin-2-yl)urea (Compound Nr 7) having a melting point of 131° C.;

N-[2-(3-methoxy-1-propyn-1-yl)phenyl]aminosulfonyl-N'-(4,6-dimethoxypyrimidin-2-yl)urea (Compound Nr 8) having a melting point of 147° C.;

N-[2-[3-(3-methoxy)-1-butyn-1-yl]phenyl]aminosulfonyl-N'-(4-methoxy-6-methyl-1,3,5-triazin-2-yl)urea (Compound Nr 9) having a melting point of 120° C.;

N-[2-[3-(3-methoxy)-1-butyn-1-yl]phenyl]aminosulfonyl-N'-(4,6-dimethoxypyrimidin-2-yl)urea (Compound Nr 10) having a melting point of 141° C.;

N-(2-bromoethynylphenyl)aminosulfonyl-N'-(4-methoxy-6-methyl-1,3,5-triazin-2-yl)urea (Compound Nr 11);

N-(2-bromoethynylphenyl)aminosulfonyl-N'-(4,6-dimethoxypyrimidin-2-yl)urea (Compound Nr 12);

N-[2-(methoxycarbonylethynyl)phenyl]aminosulfonyl-N'-(4-methoxy-6-methyl-1,3,5-triazin-2-yl)urea (Compound Nr 13);

N-[2-(methoxycarbonylethynyl)phenyl]aminosulfonyl-N'-(4,6-dimethoxypyrimidin-2-yl urea (Compound Nr 14).

EXAMPLE 4

Determination of the Herbicidal Activity and Phytotoxicity

The herbicidal activity of Compounds Nr 4 and Nr 6 with respect to some important weeds and the phytotoxicity with respect to maize and wheat were evaluated, in post-emergence treatment, compared to the N-[2-methoxycarbonylphenyl]aminosulfonyl-N'-(4,6-dimethoxypyrimidin-2-yl urea described in example 2 of the U.S. Pat. No. 4.515.620 (CR).

The evaluation tests were carried out according to the following operating procedures.

Jars (diameter of more than 10 cm, height 10 cm) containing sandy earth were prepared. In each of these one of the following weeds was sowed:

Weeds: *Abutilon theofrasti* (ABUTH), *Amaranthus retroflexus* (AMARE), *Amni maius* (AMNMA), *Convolvulus sepium* (CONSE), *Stellaria media* (STEME)

Crops: *Zea mais* (maize), Tritium sp. (wheat)

Water was added to each jar in a suitable quantity for a good germination of the seeds. The jars were divided into two groups each containing at least 5 jars for each weed.

The first group was not treated with herbicide and was used as a comparison (control).

The second group of jars was treated fifteen days after sowing in the case of the weeds and of the maize, and after ten days in the case of wheat, with a hydroacetonic dispersion at 20% by volume of acetone of the product under examination.

All the jars were kept under observation in a conditioned environment with the following environmental conditions:

temperature: 15° C.–26° C.;
relative humidity: 60%;
photoperiod: 12 hours;
luminous intensity: 5000 lux.

Every two days the jars were uniformly watered to ensure a sufficient degree of humidity for a good development of the plants.

Twenty-one days after the treatment the herbicidal activity and phytotoxicity were evaluated on the basis of the following scale of values referring to the percentage of damage found on the plants which had been treated compared to those not treated (control):
0=0%–20% of damage;
1=21%–40% of damage;
2=41%–60% of damage;
3=61%–80% of damage;
4=81%–95% of damage;
5=death of the plant treated.

The results obtained are shown in Table 1 below.

TABLE 1

HERBICIDAL ACTIVITY AND PHYTOTOXICITY IN
POST-EMERGENCE AT A DOSAGE OF 150 g/ha.

| WEED/CROP | COMPOUND Nr 4 | COMPOUND Nr 6 | REFERENCE COMPOUND CR |
|---|---|---|---|
| ABUTH | 5 | 5 | 5 |
| AMARE | 5 | 5 | 3 |
| AMNMA | 5 | 5 | 2 |
| CONSE | 5 | 5 | 3 |
| STEME | 4 | 4 | 0 |
| MAIZE | 0 | 0 | 0 |
| WHEAT | 0 | 0 | 0 |

We claim:
1. Aminosulfonyl ureas having general formula (I):

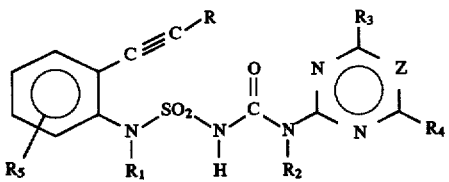

wherein:
R represents a hydrogen atom; a halogen atom; a $C_1$–$C_8$ alkyl or haloalkyl group, linear or branched; a $C_3$–$C_6$ cycloalkyl or halocycloalkyl group; a $C_4$–$C_8$ cycloalkylalkyl or halocycloalkylalkyl group; $C_2$–$C_8$ alkoxyalkyl or haloalkoxyalkyl group, linear or branched; a $C_2$–$C_8$ alkylthioalkyl or haloalkylthioalkyl group, linear or branched; a $C_2$–$C_8$ alkoxycarbonyl or haloalkoxycarbonyl group, linear or branched; a $C_2$–$C_8$ alkylaminocarbonyl group, linear or branched; a $C_3$–$C_8$ dialkylaminocarbonyl group; a $C_2$–$C_8$ alkylcarbonyl or haloalkylcarbonyl group, linear or branched; a $C_3$–$C_9$ trialkylsilyl group; a phenyl group optionally substituted by halogens, by $C_1$–$C_4$ alkyl or haloalkyl groups, linear or branched, by $C_1$–$C_4$ alkoxy or haloalkoxy groups, linear or branched, by $C_1$–$C_4$ alkylthio or haloalkylthio groups, linear or branched;

$R_1$ and $R_2$ each independently represent, a hydrogen atom; a $C_1$–$C_4$ alkyl or haloalkyl group, linear or branched; a $C_3$–$C_6$ alkoxyalkyl or haloalkoxyalkyl group, linear or branched; a $C_3$–$C_6$ alkenyl or haloalkenyl group, linear or branched; a $C_3$–$C_6$ alkynyl or haloalkenyl group, linear or branched;

$R_3$ and $R_4$ each independently represent, a hydrogen atom; a halogen atom; a $C_1$–$C_6$ alkyl or haloalkyl group, linear or branched; a $C_1$–$C_6$ alkoxy or haloalkoxy group, linear or branched; a $C_1$–$C_6$ alkylamine group, linear or branched; a $C_2$–$C_8$ dialkylamine group, linear or branched; a $C_3$–$C_6$ cycloalkyl or cycloalkoxy group; a $C_4$–$C_7$ cycloalkylalkyl or cycloalkylalkoxy group;

$R_5$ represents a hydrogen atom; a halogen atom; a $C_1$–$C_4$ alkyl or haloalkyl group, linear or branched; a $C_1$–$C_4$ alkoxy or haloalkoxy group, linear or branched;

Z represents a CH group.

2. Herbicides consisting of aminosulfonylureas having general formula

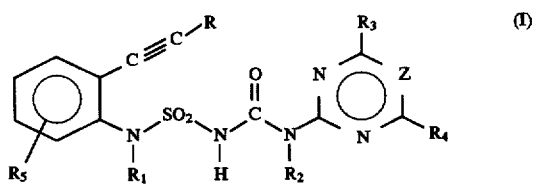

wherein:
R represents a hydrogen atom; a halogen atom; a $C_1$–$C_8$ alkyl or haloalkyl group, linear or branched; a $C_3$–$C_6$ cycloalkyl or halocycloalkyl group; a $C_4$–$C_8$ cycloalkylalkyl or halocycloalkylalkyl group; $C_2$–$C_8$ alkoxyalkyl or haloalkoxyalkyl group, linear or branched; a $C_2$–$C_8$ alkylthioalkyl or haloalkylthioalkyl group, linear or branched; a $C_2$–$C_8$ alkoxycarbonyl or haloalkoxycarbonyl group, linear or branched; a $C_2$–$C_8$ alkylaminocarbonyl group, linear or branched; a $C_3$–$C_8$ dialkylaminocarbonyl group; a $C_2$–$C_8$ alkylcarbonyl or haloalkylcarbonyl group, linear or branched; a $C_3$–$C_9$ trialkylsilyl group; a phenyl group optionally substituted by halogens, by $C_1$–$C_4$ alkyl or haloalkyl groups, linear or branched, by $C_1$–$C_4$ alkoxy or haloalkoxy groups, linear or branched, by $C_1$–$C_4$ alkylthio or haloalkylthio groups, linear or branched;

$R_1$ and $R_2$ each independently represent, a hydrogen atom; a $C_1$–$C_4$ alkyl or haloalkyl group, linear or branched; a $C_3$–$C_6$ alkoxyalkyl or haloalkoxyalkyl group, linear or branched; a $C_3$–$C_6$ alkenyl or haloalkenyl group, linear or branched; a $C_3$–$C_6$ alkynyl or haloalkenyl group, linear or branched;

$R_3$ and $R_4$ each independently represent, a hydrogen atom; a halogen atom; a $C_1$–$C_6$ alkyl or haloalkyl group, linear or branched; a $C_1$–$C_6$ alkoxy or haloalkoxy group, linear or branched; a $C_1$–$C_6$ alkylamine group, linear or branched; a $C_2$–$C_8$ dialkylamine group, linear or branched; a $C_3$–$C_6$ cycloalkyl or cycloalkoxy group; a $C_4$–$C_7$ cycloalkylalkyl or cycloalkylalkoxy group;

$R_5$ represents a hydrogen atom; a halogen atom; a $C_1$–$C_4$ alkyl or haloalkyl group, linear or branched; a $C_1$–$C_4$ alkoxy or haloalkoxy group, linear or branched;

Z represents a CH group.

3. A herbicide according to claim 2, consisting of N-[2-(3,3,3-trifluoropropynyl)phenyl]-aminosulfonyl-N'-(4,,6-dimethoxypyrimidin-2-yl)urea.

4. A herbicide according to claim 2, consisting of N-(2-ethynylphenyl)aminosulfonyl-N'-(4,6-dimethoxypyrimidin-2-yl)urea.

5. A herbicide according to claim 2, consisting of N-(2-chloroethynylphenyl)-aminosulfonyl-N'-(4,6-dimethoxypyrimidin-2-yl)urea.

6. A herbicide according to claim 2, consisting of N-[2-(3-methoxy-1-propyn-1-yl)phenyl]aminosulfonyl-N'-(4,6-dimethoxypyrimidin-2-yl)urea.

7. A process for the preparation of the aminosulfonylureas according to claim 1, comprising:

(a) reacting a heterocyclic amine having general formula (II):

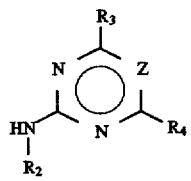

wherein $R_2$, $R_3$, $R_4$ and Z have the same meaning as defined in claim 1, with a halosulfonylisocyanate having general formula (III):

$$XSO_2NCO \quad \text{(III)}$$

wherein X represents a halogen atom in the presence of an inert organic solvent, obtaining a halosulfamoylurea having general formula (IV):

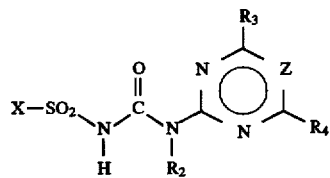

wherein X, $R_2$, $R_3$, $R_4$, and Z have the same meaning defined above;

(b) reacting the halosulfamoylurea having general formula (IV) obtained in step (a) with an aniline having general formula (V):

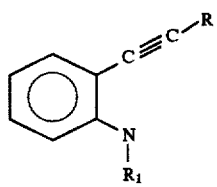

wherein R, R1 and $R_5$, have the same meaning defined above, in the presence of or without a base and an inert organic solvent.

8. The process according to claim 7, wherein the inert organic solvent which can be used in steps (a) and (b) is selected from aromatic hydrocarbons, chlorinated hydrocarbon, or ethers.

9. The process according to claim 7 wherein the organic base in step (b) is selected from aliphatic amines.

10. The process according to any of the claims from 7, wherein the above steps (a) and (b) are carried out at temperatures of between −70° C. and the boiling point of the solvent used.

11. The process according to claim 10, wherein the above steps (a) and (b) are carried out at a temperature of between −20° C. and 30° C.

12. The process according to claim 7, wherein the reaction of step (b), between the aniline having general formula (V) and the halosulfamoylurea having general formula (IV), is carried out without isolating said halosulfamoylurea (IV), by directly adding the aniline (V) and the organic base, diluted with the inert organic solvent used in step (a), operating in the same environment as the first passage.

13. Compositions with a herbicidal activity containing one or more aminosulfonylureas according to claim 2, alone or in the presence of solid carders, liquid diluents, surfactants or other active principles.

14. The compositions with a herbicidal activity according to claim 13, wherein the concentration of active substance is between 1% and 90%.

15. A method for controlling weeds in cultivated areas which consists in applying the compositions according to claims 13 to said areas.

16. The method according to claim 15, wherein the aminosulfonylureas having general formula (I) are in free or salified form.

17. The aminosulfonyl ureas according to claim 1, wherein the halogen atoms are chlorine, fluorine, bromine or iodine.

18. The herbicides according to claim 2, wherein the halogen atoms are chlorine, fluorine, bromine or iodine.

* * * * *